United States Patent [19]

Ikai et al.

[11] Patent Number: 4,712,419
[45] Date of Patent: Dec. 15, 1987

[54] AIR/FUEL RATIO DETECTOR

[75] Inventors: Tadayoshi Ikai; Takashi Kamo, both of Aichi, Japan

[73] Assignee: Toyota Jidosha Kabushiki Kaisha, Toyota, Japan

[21] Appl. No.: 862,718

[22] Filed: May 13, 1986

[30] Foreign Application Priority Data

May 13, 1985 [JP] Japan .............................. 60-70489[U]
Jun. 17, 1985 [JP] Japan .............................. 60-91090[U]

[51] Int. Cl.4 ......................................... G01M 15/00
[52] U.S. Cl. ..................................... 73/116; 204/425
[58] Field of Search ................. 73/116; 204/421, 422, 204/423, 424, 425, 426, 427, 428, 429, 408

[56] References Cited

U.S. PATENT DOCUMENTS 4,193,857 3/1980 Bannister et al. ................ 204/426 X
4,574,627 3/1986 Sakurai et al. ......................... 73/116

Primary Examiner—Jerry W. Myracle
Attorney, Agent, or Firm—Oblon, Fisher, Spivak, McClelland & Maier

[57] ABSTRACT

An air/fuel ratio detector constructed of first and second elements positioned such that the gap between the closed end of the second element constructing the limit current type oxygen sensor and the end of a tubular heater is closed or such that the one of electrodes formed on the second element and located on the side contacting the exhaust gas is made of a material having no catalytic capability to purify the exhaust gas. As a result, the second element does not constitute a concentration cell so that the output characteristics obtainable are ideal from the rich to lean range of the air-fuel ratio.

19 Claims, 14 Drawing Figures

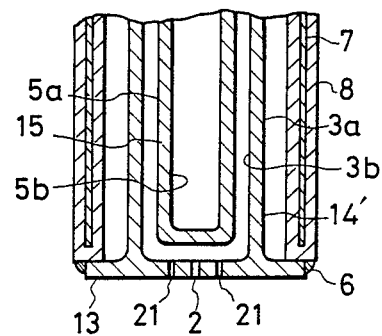
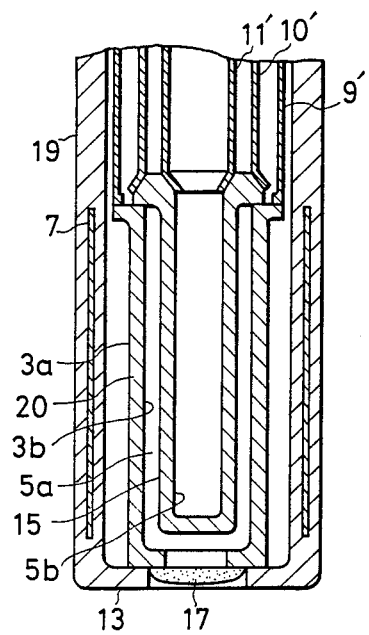
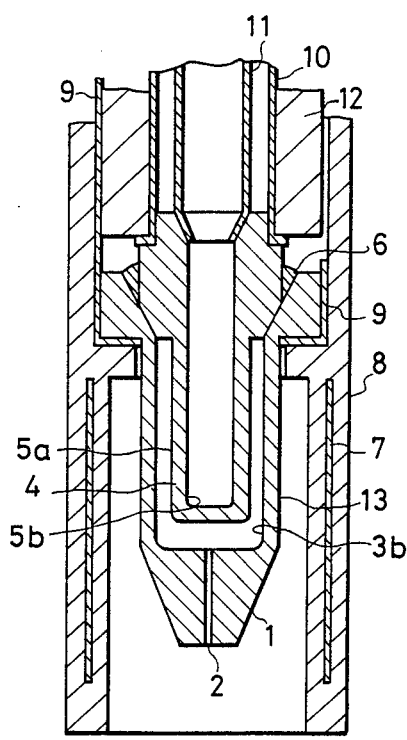
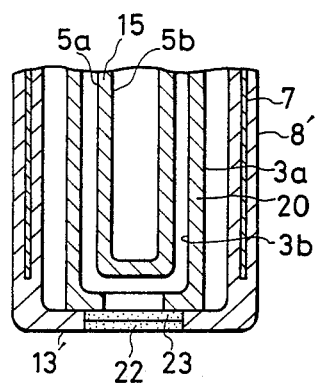

AIR/FUEL RATIO DETECTOR

BACKGROUND OF THE INVENTION

1. Field of the Invention:

The present invention relates to a detector for detecting the ratio of air to fuel, i.e., the air-fuel ratio of an internal combustion engine or the like.

2. Description of the Prior Art:

It is the current practice to detect an oxygen concentration in the exhaust gas discharged from an internal combustion engine of an automobile or the like so that the amounts of air and fuel to be fed to the internal combustion engine may be controlled on the basis of the detected value to thereby reduce the noxious content in the exhaust gas.

A known air/fuel ratio detector (or oxygen sensor) makes use of the principle of the "oxygen concentration cell" and can detect a stoichiometric air/fuel ratio (i.e., A/F=14.6) but not other regions such as a lean range in which the air/fuel ratio is higher than the stoichiometric value, or a rich range in which the air/fuel ratio is lower than this ratio. On the other hand, there has been developed a limit current type oxygen sensor for detecting the oxygen concentration by making use of a known phenomenon, and it has been investigated to detect the air/fuel ratio in the lean range. According to that phenomenon, oxygen ions will permeate from a cathode to an anode of air-permeable thin electrodes which are placed on the two sides of a solid electrolyte cell permeable to oxygen ions, if a voltage is applied between those two electrodes, so that a current will accordingly flow between the two electrodes, but the current will not increase more than a predetermined amount even with an increase of the applied voltage if the amount of permeation of the oxygen ions is restricted. The limit current type oxygen sensor is called a lean sensor because it can detect an air/fuel ratio in the lean range but can hardly detect an air/fuel ratio in the rich range.

However, in the case of the automobile, for example, it is preferable to normally run the engine in the lean range. In an uphill run requiring a higher power output, however, it is preferable to run the automobile in the rich range. It has therefore been desired to provide a detector which can cover an air/fuel ratio from the rich range to the lean range.

In order to satisfy the above-specified desire, the present Applicants have proposed an air/fuel ratio detector as shown in FIG. 13 which is a sectional view showing one example of the air/fuel detector according to the prior art. Reference numerals 1 and 4 appearing in FIG. 13 denote tubular solid electrolyte elements permeable to oxygen ions, which are equipped on their respective inner and outer sides with electrodes 3a and 3b, and 5a and 5b, made of platinum or the like. Moreover, the element 1 has its closed end formed with a gas diffusion hole 2. Numeral 6 denotes a sealing member, numeral 7 a heating element, numeral 8 a tubular heater, numerals 9, 10 and 11 leads and numeral 12 an insulating tube.

In this air/fuel ratio detector, the element 4 is used as an oxygen pump for pumping oxygen from the inside (which is vented to the atmosphere) of the element 4 into a space defined by the elements 1 and 4 so that the concentration of the residual oxygen may be detected by the element 1 acting as the limit current type oxygen sensor after the residual oxygen has reacted with the unburned content in the exhaust gas diffused through the gas diffusion hole 2.

The air/fuel detector thus constructed has output characteristics (i.e., V-I characteristics), as shown in FIG. 14. As is apparent from FIG. 14, the output characteristics, as expected, were obtained at the lean side (i.e., A/F=15 to 17) but are considerably different from the expected curves (as depicted by broken curves) at the rich side (i.e., A/F=12 to 14). This is because the space defined by the elements 1 and 4 is always fed with the oxygen from the atmosphere by the oxygen pump (i.e., the element 4) and is always held in a lean state so that the element 1 acts as a concentration cell to generate an electromotive force between the two electrodes 3a and 3b in case the exhaust gas is rich. As a result, the V-I characteristic curve at the rich side are caused to become different from the expected shapes by the influence of that electromotive force.

More specifically, the aforementioned space is fed with oxygen by the oxygen pump (i.e., the element 4). In the prior art, the electrode placed on the outer side of the element 1 is made of platinum or a material having a catalytic action for purifying the exhaust gas and is in direct contact with the exhaust gas so that the element 1 acts as the concentration cell to generate the electromotive force. Where the concentrations of the oxygen contacting with the two electrodes are very different, the element acts as the concentration cell to generate the electromotive force between its two electrodes. For example, the oxygen concentration at the side of the inner electrode of the element 1 is always held no lower than $10^{-1}$ vol % by the oxygen pump action of the element 4. When the oxygen in the rich state comes into contact with the outer electrode of the element 1, on the contrary, the oxygen concentration drops to $10^{-20}$ to $10^{-30}$ vol %, e.g., $10^{-27}$ vol % by the catalytic action of the electrode so that the element 1 acts as the concentration cell.

SUMMARY OF THE INVENTION

The present invention contemplates to solve the above-specified problems of the prior art and has as an object to provide an air/fuel ratio detector which has ideal output characteristics while preventing any electromotive force from being generated even in the rich side of air/fuel ratio, i.e., that lower than the stoichiometric ratio, between electrodes formed on the inner and outer sides of an element constructing a limit current type oxygen sensor.

According to a primary feature of the present invention, there is provided an air/fuel ratio detector having a first element of tubular shape made of an oxygen ion permeable solid electrolyte and having its one end closed and its inner and outer sides formed with electrodes which are connected with a d.c. power source to construct an oxygen pump, a second element of tubular shape made of an oxygen ion permeable solid electrolyte and having its one end closed and formed with a gas diffusion hole or layer and its inner and outer sides formed with electrodes which are connected with a voltage source to construct a limit current type oxygen sensor and a tubular heater having a heating element therein. The first element is inserted into the second element such that a first space is formed between the outer side of said first element and the inner side of said second element. The second element is inserted into said tubular heater such that a second space is formed between the outer side of the second element and the inner side of the tubular heater and such that the closed end of the second element and the end of the tubular heater are closed to close the second space.

According to a secondary feature of the present invention, there is provided an air/fuel ratio detector having a first element made of an oxygen ion permeable solid electrolyte and having its inner and outer sides formed with electrodes which are connected with a d.c. power source to construct an oxygen pump, and a second element made of an oxygen ion permeable solid electrolyte and having a gas diffusion hole or layer and its inner and outer sides formed with electrodes which are connected with a voltage source to construct a limit current type oxygen sensor. A space is formed between the outer side of said first element and the inner side of said second element and the electrode formed on the outer side of the second element is made of a material having no catalytic capability to purify an exhaust gas.

In the air/fuel ratio detector according to the primary feature of the present invention, moreover, the space between the closed end of the second element (i.e., the conventional element 1) and the end of the tubular heater is closed from the exhaust gas (but open to the atmosphere) to prevent the outer electrode of the second element from contacting directly with the exhaust gas. In order to effect this closure, an outward flange is formed on the closed end of the second element, or an inward flange is formed on the end of the tubular heater, and the second element and the tubular heater are fitted or joined together. In this case, a suitable adhesive or sealing material can be used to complete the closure. The aforementioned flanges may be formed on both the second element and the tubular heater. Moreover, no restriction is imposed on the sizes, shapes and thicknesses of the flanges. Alternatively, a suitable blind plate may be used.

Nor is any restriction imposed on the sizes and shapes of the spaces to be formed between the first element (i.e., the conventional element 4) and the second element and between the second element and the tubular heater, but their sizes and shapes are selected considering the sizes and shapes of the two elements and the tubular heater and the performance and characteristics of the air/fuel ratio detector.

Since, in the operation of the detector, the oxygen in the first space will permeate through the second element into the second space, the end of the second space opposed to the closed end may preferably be vented partially to the atmosphere.

A conventional oxygen ion permeable solid electrolyte may be used in the air/fuel ratio detector or the oxygen sensor. Specifically, the solid electrolyte to be used may be prepared by adding yttrium oxide to zirconium oxide.

The electrodes to be formed on the surface of the solid electrolyte are formed into air-permeable thin films of platinum by a known method. The electrodes are formed in a pair on the inner and outer sides of the tubular solid electrolyte such that they have corresponding areas in corresponding positions.

The gas diffusion hole may be formed by a known method such as a method of piercing a formed tube of solid electrolyte with a laser beam or a method of embedding a flammable member such as yarn in the solid electrolyte during molding and burning out the yarn during sintering to form the hole. The gas diffusion layer may be formed by a method of joining a ceramic filter to the open end of the tubular member or by a method of forming a porous ceramic coating layer on a coarsely porous ceramic member by a plasma spray coating. The gas diffusion hole and layer are formed for the same purpose as in the conventional lean sensor.

One or more diffusion holes may be formed. A plurality of output regulating holes for regulating the output of the lean sensor may be formed around the main diffusion hole and some of them filled with ceramic paste or fibers in calibrating an individual sensor.

If a catalytic metal for cleaning the exhaust gas, such as platinum, palladium or rhodium is carried in the gas diffusion layer, moreover, the pores thereof can be prevented from being clogged with carbon or the like. If desired, a component for enhancing the activity of the catalytic metal such as lanthanum, cerium, iron or nickel may be additionally provided. Such clogging is better prevented by dividing the diffusion layer into two or more sub-layers such that a coarser porous layer is disposed at the inlet side of the exhaust gas.

A heater is provided for heating the first and second elements to predetermined temperatures. The shape of the heater is not limited but may be a tubular heater containing the element therein. The material of this tubular heater is not limited but may preferably be made of an inorganic material such as refractory ceramics. The heating element to be used may be a conventional one such as a linear heating element made of nichrome wire or a planar heating element formed as a printed circuit.

In order to prevent the second element from acting as the concentration cell, in accordance with the secondary feature of the present invention the electrode to be formed on the outer side of the second element may be made of a material having an electric conductivity but not a purifying catalytic capability, such as gold (Au), silver (Ag) or silicon carbide (SiC). These materials may have any thickness or shape and may be used solely or jointly.

The size and shape of the solid electrolyte is not be limited but may be a plate or cylinder. Moreover, a heater may be provided for heating the first and second elements to predetermined temperatures.

The remaining structural elements of the air/fuel ratio detector according to the secondary feature of the present invention are similar to those of the air/fuel ratio detector according to the primary feature of the present invention.

BRIEF DESCRIPTION OF THE DRAWINGS

FIGS. 3 to 5 are sectional views showing other embodiments of the detector according to the primary feature of the present invention;

FIGS. 6 and 7 are sectional views showing the leading ends of the elements of other embodiments of the detector according to the primary feature of the present invention;

FIG. 8 is a sectional view showing one embodiment of the air/fuel ratio detector according to the secondary feature of the present invention;

DESCRIPTION OF THE PREFERRED EMBODIMENTS

The present invention will be described in more detail in the following in connection with the embodiments thereof with reference to the accompanying drawings. However, the present invention should not be limited to those embodiments.

Embodiment 1

Figure 1:
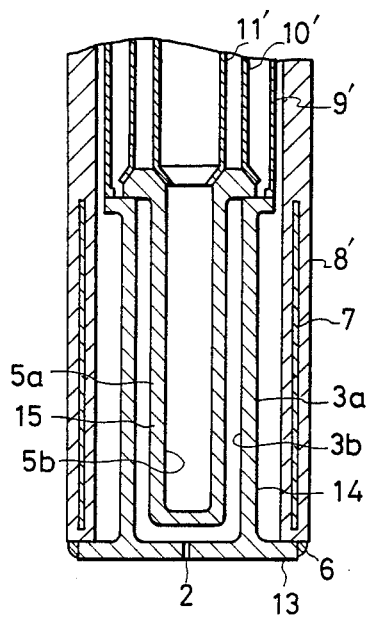
FIG. 1 is a sectional view showing one embodiment of an air/fuel detector according to the primary feature of the present invention.

FIG. 1 is a sectional view showing one embodiment of the air-fuel ratio detector according to the primary feature of the present invention. An element 14 is made of oxygen ion permeable solid electrolyte (e.g., zirconium oxide) and has its one end closed and formed with a flange 13 and a gas diffusion hole 2. Outer and inner electrodes 3a and 3b of platinum or the like are formed on the inner and outer surfaces of the element 14. Likewise, an element 15 is formed on its inner and outer sides with outer and inner electrodes 5a and 5b of platinum or the like. In this case, at least the inner electrode 3b may be catalytically activated. Then, the element 15 is inserted into the element 14. The electrodes extend by a sufficient length that, as a result, the inner electrode 3b of the element 14 and the outer electrode 5a of the element 15 are electrically connected. Then, a lead 9' for extracting charges generated on the electrode 3a to the outside is attached to the element 14, and this element 14 is inserted into a tubular heater 8' which is equipped with an internal heating element 7. The flange 13 and the end of the tubular heater 8' are fixed by means of an adhesive sealing material. A lead 10' for extracting the charges generated on the electrodes 3b and 5a to the outside and a lead 11' for extracting the charges generated on the electrode 5b to the outside are inserted into the tubular heater 8' and fixed on the element 15.

The leads 10' and 11' are connected with a d.c. constant-current power source (although not shown in the drawing) to feed the element 15 with a constant current thereby to construct an oxygen pump, by which oxygen is always fed at a constant flow rate from the inside space of the element 15 to the gap between the elements 51 and 14. Then, this oxygen is caused to react with any unburned content (e.g., hydrocarbons or carbon monoxide) in the gas to be detected which has diffused into the gap between the elements 15 and 14 through the diffusion hole 2 formed in the element 14. After this, the residual oxygen concentration is detected in terms of an output current by the limit current type oxygen sensor which is constructed by connecting the leads 9' and 10' with a d.c. constant-voltage power source (although not shown in the drawing) and by applying a constant voltage to the element 14.

Since that output current is proportional to the residual oxygen concentration which is turn is in linear relationship with the air/fuel ratio of the gas to be detected, the air/fuel ratio of the gas can be determined from the output current.

Figure 2:
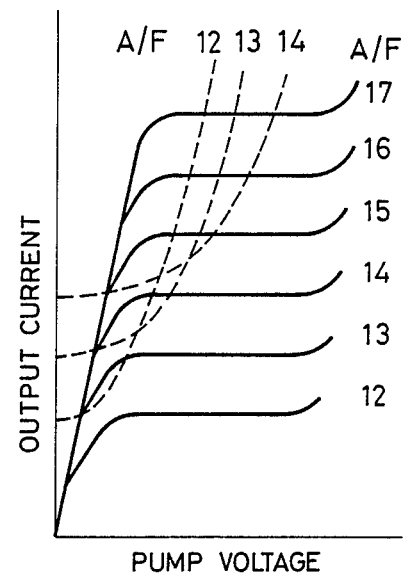
FIG. 2 is a graph depicting one example of the output characteristics of the detector of the primary feature of the present invention.

FIG. 2 depicts the output characteristics of the air/fuel ratio detector according to the present invention. In view of FIG. 2, it has been found that, in the rich range having the A/F ratio of 12 to 14, the detector of the prior art exhibits the output characteristics as plotted by broken curves, whereas the detector of the present invention exhibits the output characteristics as plotted by solid curves, even when the exhaust gas is in a rich state, because the electrode 3a is kept out of contact with the exhaust gas. Thus, the output characteristics are ideal from the rich range to the lean range.

Embodiment 2

Figure 3:
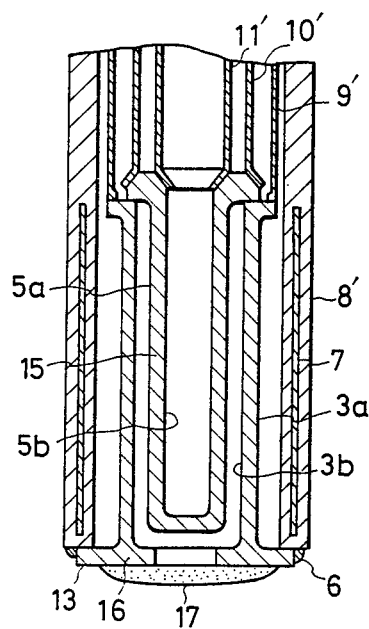

The leading end of the element according to another embodiment of the present invention is shown in section in FIG. 3. An element 16 is formed with a gas diffusion layer 17 made of a ceramic coating layer in place of the gas diffusion hole. In this case, the temperature dependency of the output can be eliminated by adjusting the mean pore diameter of the gas diffusion layer.

Embodiment 3

Figure 4:
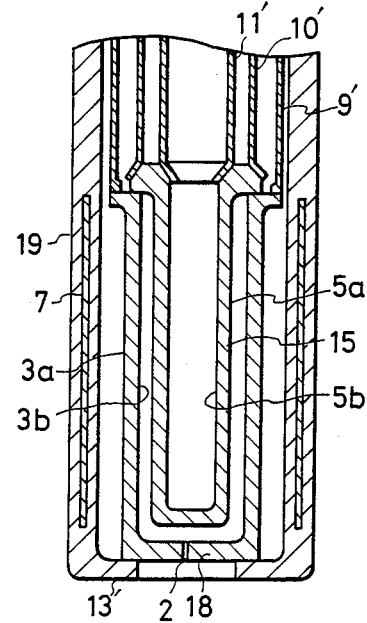

FIG. 4 is a sectional view showing a portion of the element according to still another embodiment of the present invention. An element 18 is inserted into a tubular heater 19 which is formed with an inward flange 13' at its end so that its leading end opening has an internal diameter smaller than the external diameter of the closed end of the element 18. The element 18 is fixed by pressing it downwardly with element 5.

Embodiment 4

FIG. 5 is a sectional view showing a portion of the element according to a further embodiment of the present invention. An element 20 is formed as in the embodiment 3 and also includes the gas diffusion layer 17 of a ceramic coating layer in place of the gas diffusion hole, as in embodiment 2.

Embodiment 5

FIG. 6 is a sectional view showing a leading end portion of the element according to a further embodiment of the present invention. Output regulating holes 21 are formed around the diffusion hole 2. The output regulating holes 21 are filled with ceramic paste or the like, preferably symmetrically with respect to the diffusion hole 2 in accordance with a variance of the output of the element from the standard output during calibration of the element.

Embodiment 6

FIG. 7 is a sectional view showing the leading end portion of the element according to a further embodiment of the present invention. This embodiment is similar to that of FIG. 5 except that the diffusion layer is divided into two sub-layers. Of these, the sub-layer located at the inlet side of the gas to be detected is equipped with a ceramic filter 22 having larger pores and the other is equipped with a ceramic filter 23 having smaller pores. On these ceramic filters, there can be carried a catalytic metal for purifying the exhaust gas.

Embodiment 7

FIG. 8 is a sectional view showing one embodiment of the air/fuel ratio detector according to the secondary feature of the present invention. An element 1 is made of oxygen ion permeable solid electrolyte (e.g., zirconium oxide) and has its one end closed, except for diffusion hole 2. The element 1 has on its outer surface an outer electrode 13 of a material having no catalytic action to purify the exhaust gas, such as Au, Ag or SiC, and on its inner surface an inner electrode 3b of platinum or the like. Likewise, an element 4 is formed on its inner and outer surfaces with outer and inner electrodes 5a and 5b of platinum or the like. In this case, at least the electrode 3b of the platinum electrodes may preferably be catalytically activated. Next, the element 4 is inserted into the element 1, and the gap therebetween is filled with a sealing material such as glass. At this time, the inner electrode 3b of the element 1 and the outer electrode 5a of the element 4 are electrically connected. Next, a lead 9 for extracting charges generated on the electrode 13 to the outside is attached to the element 1, and this element 1 is inserted into a tubular heater 8 having an interior heating element 7. Moreover, a lead 10 for extracting the charges generated on the electrodes 3b and 5a to the outside, a lead 11 for extracting the charges generated on the electrode 5b to the outside, and an insulating tube 12 are inserted into the tubular heater 8 to fix the elements 1 and 4.

The leads 10 and 11 are connected with a d.c. constant current power source (although not shown in the drawing) to feed a constant current to the element 4 to thereby construct an oxygen pump, by which oxygen is always fed at a constant flow rate from an internal space of the element 4 to the gap between the elements 1 and 4. This oxygen is caused to react with any unburned content (e.g., hydrocarbons or carbon monoxide) in the gas to be detected that has diffused into the gap between the elements 1 and 4 through the diffusion hole 2 formed in the element 1. After this, the concentration of the residual oxygen is detected in terms of an output current by means of the limit current type oxygen sensor which is constructed by connecting the leads 9 and 10 with a d.c. constant voltage power source (although not shown in the drawing) and by applying a constant voltage to the element 1.

Since this output current is proportional to the residual oxygen concentration which in turn is in a linear relationship with the air/fuel ratio of the gas to be detected, the air/fuel ratio of the gas to be detected can be determined from that output current.

The output characteristics of the air/fuel ratio detector according to the secondary feature of the present invention are similar to those of the air/fuel ratio detector according to the primary feature of the present invention, as shown in FIG. 2, and are ideal from the rich range to the lean range.

Embodiment 8

Figure 9:
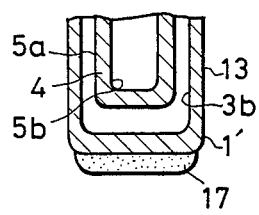
FIGS. 9 to 11 are sectional views showing the leading ends of other embodiments of the detector according to the secondary feature of the present invention.

The leading end portion of the element according to another embodiment of the present invention is shown in section in FIG. 9. An element 1' is formed with the gas diffusion layer 17 made of a ceramic coating layer in place of the gas diffusion hole. In this case, the temperature dependency of the output can be eliminated by controlling the mean pore diameter of the gas diffusion layer. Incidentally, the ceramic coating layer need not always be limited to the leading end of the element but may extend over the entire electrode 13.

Embodiment 9

Figure 10:
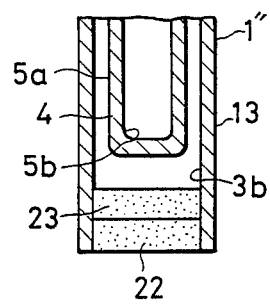

FIG. 10 is a sectional view showing a portion of the element according to still another embodiment of the present invention. The diffusion layer is divided into two sub-layers. Of these, the sub-layer located at the inlet side of the gas to be detected is equipped with the ceramic filter 22 having a larger pore diameter, and the other sub-layer is equipped with the ceramic filter 23 having a smaller pore diameter. On these ceramic filters, there can be carried a catalytic metal for purifying the exhaust gas.

Embodiment 10

Figure 11:
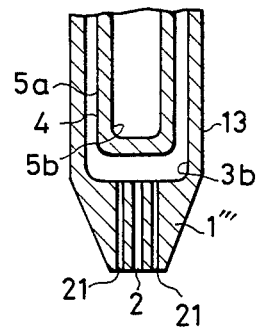

FIG. 11 is a sectional view showing a portion near the diffusion hole of the element according to a further embodiment of the present invention. The output regulating holes 21 are formed around the diffusion hole 2. The output regulating holes 21 are filled with ceramic paste or the like, preferably symmetrically with respect to the diffusion hole 2, in accordance with a variance of the output of the element from the standard output during calibration of the element.

Embodiment 11

Figure 12:
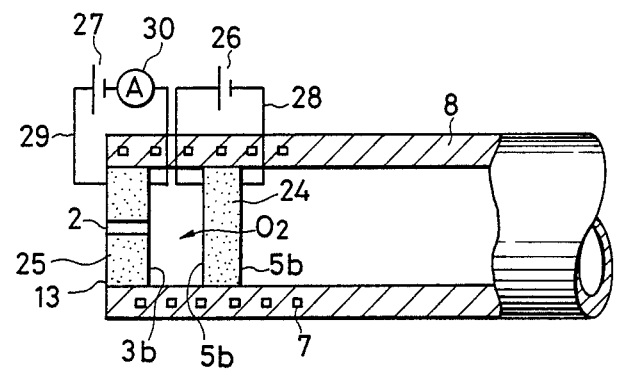
FIG. 12 is a sectional view showing another embodiment of the detector according to the secondary feature of the present invention.
Figure 13:
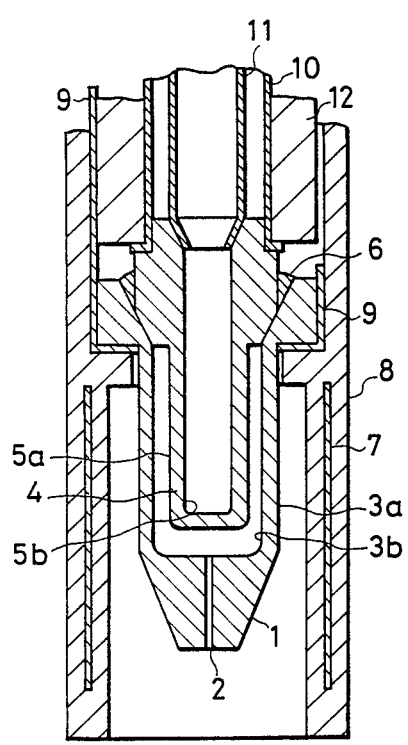
FIG. 13 is a sectional view showing one example of the air/fuel ratio detector of the prior art.
Figure 14:
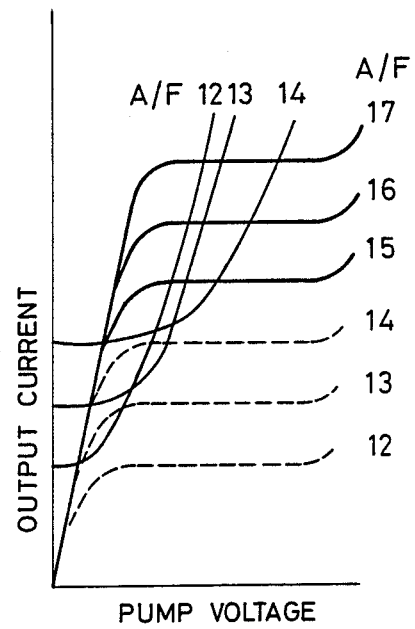
FIG. 14 is a graph depicting one example of the output characteristics of the detector of the prior art.

FIG. 12 shows a further embodiment of the present invention using plate-shaped elements. In FIG. 12 reference numerals 24 and 25 denote the plate-shaped elements, numeral 26 a constant-current power source, numeral 27 a constant-voltage power source, numerals 28 and 29 leads, numeral 30 a current meter and the remaining numerals denote the same components as those of the foregoing embodiments.

As has been described hereinbefore, the air/fuel ratio detector according to the present invention is constructed such that the gap between the closed end of the element constructing the limit current type oxygen sensor and the end of the tubular heater is closed or such that, of the electrodes to be formed on the element constructing the limit current type oxygen sensor, the electrode on the side contacting the exhaust gas is made of a material having no catalytic capability to purify the exhaust gas. In contrast to the prior art, therefore, the aforementioned element does not constitute a concentration cell so that no discrepancy of the output characteristic curves from the expected ones is caused in the (rich) range in which the air/fuel ratio is smaller than the stoichiometric value. As a result, the output characteristics are ideal from the rich range to the lean range to greatly improve the reliability and controllability of the air/fuel ratio detector.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An air/fuel ratio detector comprising:
    a first element of tubular shape made of an oxygen ion permeable solid electrolyte and having one end closed and inner and outer sides formed with electrodes which are connected with a d.c. power source to form an oxygen pump;
    a second element of tubular shape made of an oxygen ion permeable solid electrolyte and having one end formed with gas diffusion means, inner and outer sides of said second element being formed with electrodes which are connected with a voltage source to form a limit current type oxygen sensor; and
    a tubular heater having a heating element therein,
    wherein said first element is inserted into said second element such that a first space is formed between an outer side of said first element and an inner side of said second element, wherein said second element is inserted into said tubular heater such that a second space is formed between the outer side of said second element and the inner side of said tubular heater and wherein said one end of said second element and an end of said tubular heater include means to seal said second space.

2. An air/fuel ratio detector according to claim 1, wherein said solid electrolyte is made of zirconium oxide.

3. An air/fuel ratio detector according to claim 1, wherein said electrodes are made of platinum.

4. An air/fuel ratio detector according to claim 1, wherein said gas diffusion means comprise at least one hole.

5. An air/fuel ratio detector according to claim 1, wherein said gas diffusion means comprise a gas diffusion layer made from at least one from the group consisting of a ceramic porous material and a porous ceramic coating layer.

6. An air/fuel ratio detector according to claim 5, wherein said gas diffusion layer carries thereon a catalytic metal for purifying the exhaust gas.

7. An air/fuel ratio detector according to claim 5, wherein said gas diffusion layer is composed of at least two sub-layers having different pore diameters.

8. An air/fuel ratio detector according to claim 1, wherein said tubular heater is a ceramic heater.

9. An air/fuel ratio detector according to claim 1, wherein said heating element is one of a linear and planar heating element.

10. An air/fuel ratio detector according to claim 1, wherein said means to seal said second space comprise an outward flange formed on said one end of said second element and abutting against said end of said tubular heater.

11. An air/fuel ratio detector according to claim 1, wherein said electrode of said first element outer side and said electrode of said second element inner side are mutually electrically connected.

first element made of an oxygen ion permeable solid

12. An air/fuel ratio detector comprising:
a first element made of an oxygen ion permeable solid electrolyte and having inner and outer sides formed with electrodes which are connected with a d.c. power source to form an oxygen pump; and
a second element made of an oxygen ion permeable solid electrolyte and having gas diffusion means, inner and outer sides of said second element being formed with electrodes which are connected with a voltage source to form a limit current type oxygen sensor, wherein said gas diffusion means comprise a gas diffusion layer made from at least one from the group consisting of a ceramic porous material and a porous ceramic coating layer, and formed of at least two sub-layers having different pore diameters,
wherein said first and second elements are mutually positioned such that a space is formed between the outer side of said first element and the inner side of said second element, and wherein the electrode formed on the outer side of said second element is made of a material having no gas purifying catalytic capability.

13. An air/fuel ratio detector according to claim 12, wherein said solid electrolyte is made of zirconium oxide.

14. An air/fuel ratio detector according to claim 12, wherein elecrodes other than said electrode formed on the outer side of said second element are made of platinum.

15. An air/fuel ratio detector according to claim 12, wherein said gas diffusion means comprise at least one hole.

16. An air/fuel ratio detector according to claim 12, wherein said gas diffusion layer carries thereon a catalytic metal for purifying the exhaust gas.

17. An air/fuel ratio detector according to claim 12, further comprising a heater for heating said first and second elements.

18. An air/fuel ratio detector according to claim 12, wherein the material having no catalytic capability to purify the exhaust gas is at least one selected from the group consisting of gold, silver and silicon carbide.

19. An air/fuel ratio detector according to claim 12, wherein said electrode of said first element outer side and said electrode of said second element inner side are mutually electrically connected.

* * * * *